US010839201B2

United States Patent
Johnson et al.

(10) Patent No.: US 10,839,201 B2
(45) Date of Patent: Nov. 17, 2020

(54) FACIAL EXPRESSION DETECTION FOR SCREENING AND TREATMENT OF AFFECTIVE DISORDERS

(71) Applicant: Akili Interactive Labs, Inc., Boston, MA (US)

(72) Inventors: Jason Johnson, Novato, CA (US); Jason Trees, Dedham, MA (US); Elena Cañadas Espinosa, Dorchester, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 0 days.

(21) Appl. No.: 16/681,711

(22) Filed: Nov. 12, 2019

(65) Prior Publication Data

US 2020/0151439 A1 May 14, 2020

Related U.S. Application Data

(60) Provisional application No. 62/758,461, filed on Nov. 9, 2018.

(51) Int. Cl.
*G06K 9/00* (2006.01)
*A61B 5/16* (2006.01)
(Continued)

(52) U.S. Cl.
CPC .......... *G06K 9/00315* (2013.01); *A61B 5/163* (2017.08); *A61B 5/165* (2013.01);
(Continued)

(58) Field of Classification Search
None
See application file for complete search history.

(56) References Cited

U.S. PATENT DOCUMENTS 9,147,107 B2 9/2015 Kaneda
9,311,680 B2 4/2016 Kim
(Continued)

FOREIGN PATENT DOCUMENTS

WO 2018128996 A1 7/2018

OTHER PUBLICATIONS

Regan Mandryk, A continuous and objective evaluation of emotional exprerience with interactive play environments, Jan. 2006, CCHI 2006 Proceedings. Conference paper. (Year: 2006).*
(Continued)

*Primary Examiner* — Iman K Kholdebarin
(74) *Attorney, Agent, or Firm* — Gregory Finch; Finch Paolino, LLC

(57) ABSTRACT

Embodiments of the present disclosure provide a system and method for using facial recognition and mimicry workflows to train cognitive and emotional empathy. The system and methods comprise the use of physiological measurements (e.g., EEG, etc.) in combinations with facial recognition to detect user affect and modify one or more cognitive screening instruments to further promote a user affect. One or more specific emotions associated with one or more specific negative cognitive bias are targeted to influence affect. One or more specific psychopathology may be treated using an emotional recognition training component within a computerized cognitive-bias modification regimen. The regimen may comprise the identification, targeting, and modification of emotions and may utilize one or more facial inputs, cognitive tasks, facial recognition and facial mimicry protocols to adaptively modify one or more attributes of one or more computerized stimuli or interactions within a computerized platform or platform-product.

19 Claims, 12 Drawing Sheets

(51) Int. Cl.
  *G06K 9/66* (2006.01)
  *G06Q 30/02* (2012.01)
  *G16H 50/20* (2018.01)
(52) U.S. Cl.
  CPC .............. *G06K 9/66* (2013.01); *G06Q 30/02* (2013.01); *G16H 50/20* (2018.01)

(56) References Cited

U.S. PATENT DOCUMENTS

| | | | |
|---|---|---|---|
| 9,934,426 B2 | 4/2018 | Kim et al. | |
| 2011/0263946 A1* | 10/2011 | el Kaliouby | G06K 9/00335 600/300 |
| 2013/0226464 A1* | 8/2013 | Marci | A61B 5/16 702/19 |
| 2014/0148728 A1* | 5/2014 | Eizenman | A61B 5/4848 600/558 |
| 2014/0192325 A1* | 7/2014 | Klin | A61B 3/0041 351/209 |
| 2014/0200416 A1 | 7/2014 | Kashef et al. | |
| 2014/0315168 A1* | 10/2014 | Movellan | G16H 50/20 434/236 |
| 2014/0316881 A1* | 10/2014 | Movellan | G06K 9/00315 705/14.42 |
| 2014/0323817 A1* | 10/2014 | el Kaliouby | G16H 20/70 600/300 |
| 2015/0157259 A1* | 6/2015 | Bradu | A61B 5/4519 600/476 |
| 2015/0206000 A1* | 7/2015 | el Kaliouby | H04L 51/02 382/118 |
| 2016/0063874 A1* | 3/2016 | Czerwinski | G06Q 10/107 434/236 |
| 2016/0078279 A1* | 3/2016 | Pitre | G06T 7/11 382/118 |
| 2017/0238860 A1* | 8/2017 | el Kaliouby | A61B 5/1176 |
| 2017/0344891 A1 | 11/2017 | Akazawa et al. | |
| 2018/0126117 A1* | 5/2018 | Bar-Haim | A61B 5/163 |
| 2018/0184964 A1* | 7/2018 | Simon | A61B 5/0482 |
| 2018/0189398 A1 | 7/2018 | Sternberg et al. | |
| 2018/0374498 A1 | 12/2018 | Nomura et al. | |
| 2019/0159716 A1* | 5/2019 | Alailima | A61B 5/1124 |
| 2019/0268660 A1* | 8/2019 | el Kaliouby | G06K 9/00845 |
| 2020/0074154 A1* | 3/2020 | el Kaliouby | G06K 9/00288 |

OTHER PUBLICATIONS

International Search Report and Written Opinion of the International Searching Authority, International Application No. PCT/US19/61011, dated Feb. 5, 2020. ISA/US, Alexandria, Virginia.

Dalili, Michael N., et al., "Emotion recognition training using composite faces generalises across dentities but not all emotions." Cognition and Emotion, 2017. vol. 31, No. 5, 858-867. Routledge Taylor & Francis Group, Abingdon, UK.

Penton-Voak, Ian, et al. "Increasing Recognition of Happiness in Ambiguous Facial Expressions Reduces Anger and Aggressive Behavior." Psychological Science, 24(5), 688-697, Mar. 26, 2013. Published online at https://journals.sagepub.com/doi/10.1177/0956797612459657. Sage Journals, Thousand Oaks, CA.

* cited by examiner

ND TREATMENT OF
FACIAL EXPRESSION DETECTION FOR SCREENING AND TREATMENT OF AFFECTIVE DISORDERS

CROSS REFERENCE TO RELATED APPLICATIONS

This application claims priority benefit of U.S. Provisional Application Ser. No. 62/758,461 filed Nov. 9, 2018, the entirety of which is hereby incorporated herein at least by reference.

FIELD

The present disclosure relates to the field of computer-assisted therapeutic treatments; in particular, a facial image processing system and method for screening and treatment of certain psychopathologies involving cognition and affect.

BACKGROUND

Stress, anxiety, and other kinds of emotion can profoundly influence key elements of cognition, including selective attention, working memory, and cognitive control. Affect is a concept used in psychology to describe the experience of feeling or emotion. Affect mediates an organism's interaction with stimuli. Affect is sometimes referred to as an affect display or an indicator which is a facial, vocal, or gestural behavior. In certain perspectives, cognition may be considered as a part of the affective, or vice versa. Many of the most common psychopathologies; depression, schizophrenia, substance abuse, chronic pain, and autism, involve prominent disturbances of cognition and emotion. For example, a core deficit in autism-spectrum conditions is decreased cognitive empathy. These neurodevelopmental conditions may be characterized by impairments in social communication and interaction, as well as restricted interests and repetitive behavior.

Adaptive bias is the idea that the human brain has evolved to reason adaptively, rather than truthfully or even rationally. Cognitive bias may have evolved as a mechanism to reduce the overall cost of cognitive errors rather than reducing the number of cognitive errors, when faced with decision-making under conditions of uncertainty. Cognitive-bias modification (CBM) techniques are designed to modify the cognitive biases characteristic of a number of psychopathologies such as depression and social anxiety. Since these biases are thought to be involved in the maintenance of these disorders, CBM techniques attempt to modify maladaptive cognitive biases, or induce adaptive biases. CBM designed to change attentional selectivity has proven capable of modifying attentional biases associated with emotional dysfunction. CBM designed to change interpretive selectivity has proven capable of modifying the tendency to resolve ambiguity in a negative manner that is characteristic of emotional dysfunction.

Emotion recognition training (ERT) is a CBM task used to shift the biased perception of neutral or ambiguous faces, characteristic of many disorders, from negative to more positive. ERT has shown promise in improving affect in individuals suffering from low mood. However, ERT does not simply induce a general positivity bias. In order for CBM to be most effective, the accurate identification and targeting of specific emotions are required in the maintenance of mental illnesses.

Cognitive empathy describes a person's ability to infer the mental states of others, while emotional empathy is defined as an observer's emotional response to another individual's emotional state. Cognitive empathy is conceptually linked with emotion recognition. Humans often react to the emotional expressions of others with spontaneous imitation. Facial expressions that match the expressed emotion of the counterpart have been labelled "facial mimicry" and are considered central for social interactions. Studies have shown that people tend to mimic the valence of emotions rather than discrete emotions. Valence in this context broadly refers to the intrinsic attractiveness or averseness of an event, object, or situation. Mimicking another person's facial emotional expression has been shown to foster a shared emotional state in the observer. There are increasing clinical findings to support the view that mimicry is primarily an affiliative response to an emotional signal in social interaction.

The need exists for more effective means of training affect by targeting emotion with accuracy and specificity in cognitive-bias modification interventions. Through applied effort, ingenuity, and innovation, Applicant has identified deficiencies of the conventional approaches towards treatments and interventions for disturbances of cognition and emotion and has developed a solution that is embodied by the present invention, which is described in detail below.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Certain aspects of the present disclosure provide for a computer-implemented method for facial image processing, comprising providing, with a computing device comprising a user interface, an instance of a computerized stimuli or interaction comprising an emotional expression prompt; receiving, with a camera being operably engaged with the computing device, a digital image of a facial expression of a user in response to the computerized stimuli or interaction; processing, with at least one processor, the digital image to determine a valence input and an intensity or arousal input corresponding to the emotional expression; comparing, with the at least one processor, the valence input and the intensity or arousal input to a predetermined valence and intensity/arousal range associated with the emotional expression prompt; and determining, with the at least one processor, a measure of concordance between the facial expression of the user and the emotional expression prompt.

Certain embodiments of the computer-implemented method for facial image processing may be further configured wherein the emotional expression prompt comprises presenting an image or icon representative of an emotional expression and prompting the user to mimic the emotional expression.

Certain embodiments of the computer-implemented method for facial image processing may further comprise determining, with the processor, a measure of a cognitive bias or an affective state of the user according to the measure of concordance between the facial expression of the user and the emotional expression prompt.

Certain embodiments of the computer-implemented method for facial image processing may further comprise measuring, with at least one physiological sensor, at least one physiological input concomitantly with receiving the digital image of the facial expression of the user in response to the emotional expression prompt.

Certain embodiments of the computer-implemented method for facial image processing may further comprise providing, with the computing device, a second or subsequent instance of the computerized stimuli or interaction according to the measure of concordance between the facial expression of the user and the emotional expression prompt. In certain embodiments, the computerized stimuli or interaction is associated with a computerized cognitive-bias modification regimen.

Certain embodiments of the computer-implemented method for facial image processing may further comprise modifying, with the processing device, a second or subsequent instance of the computerized stimuli or interaction according to the cognitive bias or the affective state of the user.

Certain embodiments of the computer-implemented method for facial image processing may further comprise determining, with the processing device, an affective state of the user according to the at least one physiological input.

Certain embodiments of the computer-implemented method for facial image processing may further comprise modifying, with the processing device, a second or subsequent instance of the computerized stimuli or interaction according to the affective state of the user.

Certain embodiments of the computer-implemented method for facial image processing may further comprise determining, with the processing device, a measure of change in the cognitive bias or affective state of the user in response to the second or subsequent instance of the computerized stimuli or interaction.

Certain aspects of the present disclosure provide for a system for facial image processing, comprising a computing device comprising a camera configured to receive a digital image of a facial expression of a user in real-time; an integral or remote processor communicatively engaged with the computing device; and a non-transitory computer readable medium having instructions stored thereon that, when executed, cause the processor to perform one or more operations, the one or more operations comprising rendering an instance of a computerized stimuli or interaction comprising an emotional expression prompt to the computing device; receiving a real-time digital image of a facial expression of a user in response to the computerized stimuli or interaction; processing the digital image to determine a valence input and an intensity input corresponding to the emotional expression; comparing the valence input and the intensity input to a predetermined valence and intensity range associated with the emotional expression prompt; and determining a measure of concordance between the facial expression of the user and the emotional expression prompt.

Certain embodiments of the computer-implemented system for facial image processing may further comprise at least one physiological sensor operably engaged with the processor to measure at least one physiological sensor input in response to the computerized stimuli or interaction.

Certain embodiments of the computer-implemented system for facial image processing may be further configured wherein the emotional expression prompt comprises rendering an image or icon representative of an emotional expression and prompting the user to mimic the emotional expression.

Certain embodiments of the computer-implemented system for facial image processing may be further configured wherein the one or more operations further comprise determining a measure of a cognitive bias or an affective state of the user according to the measure of concordance between the facial expression of the user and the emotional expression prompt.

Certain embodiments of the computer-implemented system for facial image processing may be further configured wherein the one or more operations further comprise rendering a second or subsequent instance of the computerized stimuli or interaction according to the measure of concordance between the facial expression of the user and the emotional expression prompt.

Certain embodiments of the computer-implemented system for facial image processing may be further configured wherein the one or more operations further comprise modifying a second or subsequent instance of the computerized stimuli or interaction according to the cognitive bias or the affective state of the user.

Certain embodiments of the computer-implemented system for facial image processing may be further configured wherein the one or more operations further comprise modifying a second or subsequent instance of the computerized stimuli or interaction according to the at least one physiological sensor input.

Certain embodiments of the computer-implemented system for facial image processing may be further configured wherein the one or more operations further comprise modifying a second or subsequent instance of the computerized stimuli or interaction according to the measure of concordance between the facial expression of the user and the emotional expression prompt.

Certain embodiments of the computer-implemented system for facial image processing may be further configured wherein the one or more operations further comprise determining a measure of change in the cognitive bias or affective state of the user in response to the second or subsequent instance of the computerized stimuli or interaction.

Still further aspects of the present disclosure provide for a non-transitory computer-readable medium encoded with instructions for commanding one or more processors to execute operations of a method for facial image processing, the operations comprising providing a first instance of a computerized stimuli or interaction comprising an emotional expression prompt to an output device; receiving a digital image of a facial expression of a user in response to the emotional expression prompt; processing the digital image to determine a valence input and an intensity input corresponding to the facial expression; comparing the valence input and the intensity input to a predetermined valence and intensity range associated with the facial expression prompt; and determining a measure of concordance between the facial expression of the user and the emotional expression prompt.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The above and other objects, features and advantages of the present disclosure will be more apparent from the following detailed description taken in conjunction with the accompanying drawings, in which.

DETAILED DESCRIPTION

Figure 1:
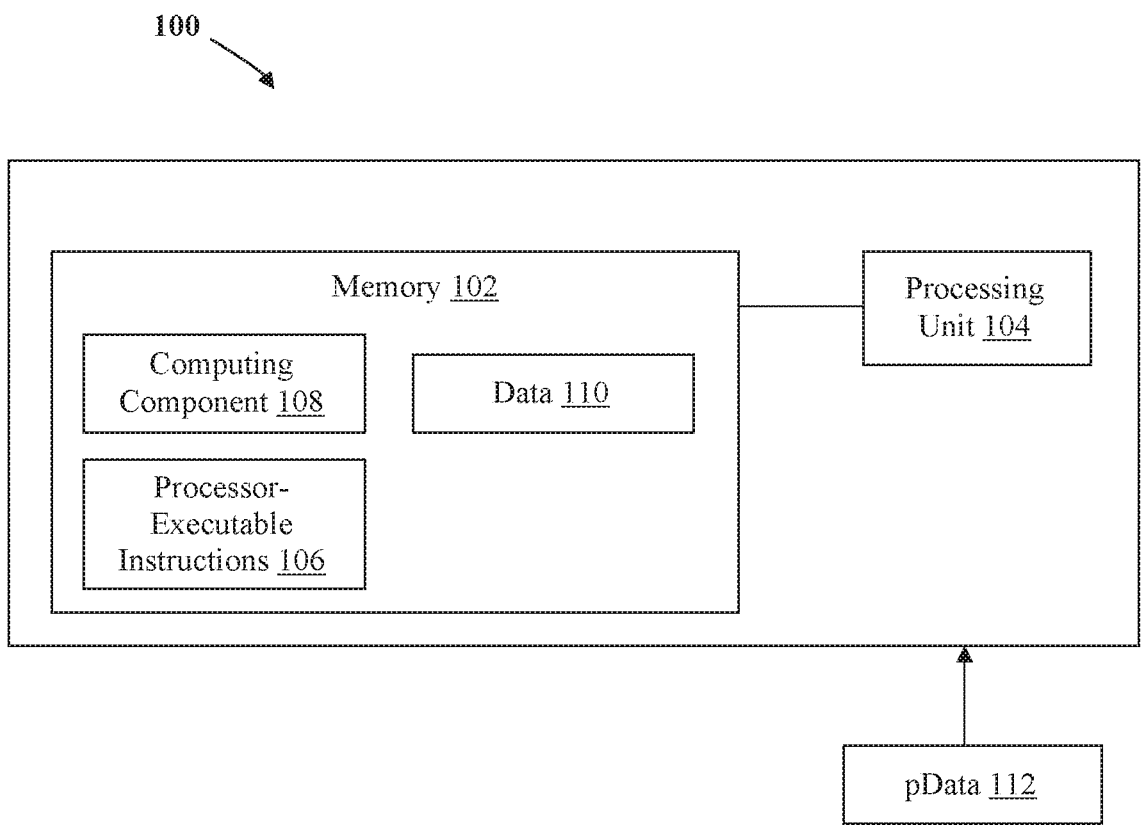
FIG. 1 is a functional block diagram of an exemplary computing device in which one or more aspects of the present disclosure may be implemented.

Aspects of the present disclosure provide for systems and methods comprising facial recognition and mimicry workflows to train cognitive and emotional empathy. In various embodiments, the system comprises a facial image processor further comprising a computing device and at least one camera configured to receive one or more digital image of at least one facial expression of a user, preferably in real-time. In one embodiment, the computing device comprises an integral computing processor, including but not limited to, a processor, microprocessor, or the like. In an alternative embodiment, the computing device engages communicatively with a remote computing processor, microprocessor, or the like. In various embodiments, the facial image processor comprises a non-transitory computer readable medium having stored instructions for causing the processor to perform one or more operations. In various embodiments, the operations comprise, rendering one or more, first, second, or subsequent instance of a computerized stimuli or interaction (CSI) comprising one or more facial expression prompt, image, icon, or the like, to the computing device, receiving preferably in real-time, one or more digital images of a facial expression of a user in response to the computerized stimuli or interaction, processing the digital image to determine a valence input and an intensity input corresponding to the facial expression, comparing the valence input and the intensity input to a predetermined valence and intensity range associated with the facial expression prompt, and determining a measure of concordance between the between the facial expression of the user and the facial expression prompt.

Aspects of the present disclosure provide for a system and methods comprising at least one physiological sensor (e.g., EEG) to measure at least one physiological sensor input in response to the computerized stimuli or interaction. In various embodiments, the one or more operations further comprise determining a measure of a cognitive bias or an affective state of the user according to the measure of concordance between the facial expression of the user and the facial expression prompt. In various embodiments, the method comprises the use of physiology measurements (e.g., EEG, fMRI, etc.) and/or facial recognition technology to detect one or more emotion or affective state in the user with accuracy and specificity. In various embodiments, one or more CSIs are adapted to further target one or more specific emotion or cognitive bias and modify or optimize an affective state of the user.

Aspects of the present disclosure further provide for systems and methods to improve, optimize or otherwise influence affect in a user comprising a computer-implemented method to target specific emotions associated with a specific negative cognitive bias. In various embodiments, the specific negative cognitive bias is associated with a specific psychopathology. In various embodiments, the computer-implemented method comprises a digital camera operably engaged with a facial image processing engine. Certain embodiments may further comprise a computing device having a user interface configured to provide one or more instances of an emotional expression prompt. In certain embodiments, the instance of the emotional expression prompt is embodied a computerized interaction. In various embodiments, the computer-implemented method comprises receiving one or more digital image, via at least one camera, of a facial expression of a user, in response to the computerized stimuli or interaction. In various embodiments, the method comprises steps for processing said digital image to determine one or more valence input and/or one more intensity or arousal input corresponding to a facial expression of the user. In various embodiments, the method comprises steps for comparing the valence and/or intensity input to a predetermined valence or intensity value range associated with a facial expression image, icon, or prompt, and determining a measure of concordance between the user's facial expression and the facial expression image, icon, or prompt. In various embodiments, the method comprises steps for determining a measure of a user's cognitive bias or an affective state. In various embodiments, the method comprises steps for measuring with at least one physiology measurement (e.g., EEG, fMRI, etc.) concomitantly with a digital image, icon, or facial expression of the user in response to the facial image, icon, or facial expression prompt. In one embodiment, one or more physiological measurement enables the determination of an affective state of a user. In various embodiments, the method comprises steps of providing one or more, first, second, or subsequent instance of a computerized stimuli or interaction comprising one or more facial expression prompt, image, icon, or the like. In one embodiment, the computerized stimuli or interaction comprises a computerized cognitive-bias modification regimen. In various embodiments, the method comprises steps of modifying, with the processing device, one or more, first, second, or subsequent instance of a computerized stimuli or interaction according to the cognitive bias, affective state, and/or a measure of change of the cognitive bias or affective state of a user.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems comprising a cognitive, emotional mimicry empathy recognition and training platform and/or platform product configured for coupling with one or more other types of measurement components (e.g., EEG, fMRI, etc.), and for analyzing data collected from user interaction with the cognitive, emotional mimicry empathy recognition and training platform and/or from at least one measurement of the one or more other types of components. As non-limiting examples, an affective modification or emotional recognition training platform and/or platform product can be configured for cognitive and emotional training, treatment, clinical, or interventional purposes.

In an example implementation, the affective modification or emotional recognition training platform may be integrated with one or more physiological or monitoring components and/or cognitive testing components.

In another example implementation, the affective modification or emotional recognition training platform may be separate from, and configured for coupling with, the one or more physiological or monitoring components and/or cognitive testing components.

In any example herein, the affective modification or emotional recognition training platform system and methods can be configured to present computerized tasks and platform interactions that inform cognitive or emotion assessment (including screening and/or monitoring) or to deliver treatment, therapy, or intervention.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The example methods, apparatus and systems comprising the cognitive, emotional mimicry empathy recognition and training platform or platform product can be used by an individual, of a clinician, a physician, and/or other medical or healthcare practitioner to provide data that can be used for an assessment of the individual.

In non-limiting examples, the methods, apparatus and systems comprising the affective modification or emotional recognition training platform or platform product can be configured as a monitoring tool to detect differences in cognition and emotion and for training, treating, or intervention in normal individuals, individual with disturbances of cognition and emotion, or individuals diagnosed with common neuropsychiatric disorders, including but not limited to, depression, schizophrenia, substance abuse, chronic pain, autism, dementia, Parkinson's disease, cerebral amyloid angiopathy, familial amyloid neuropathy, Huntington's disease, or other neurodegenerative condition, autism spectrum disorder (ASD), presence of the 16p11.2 duplication, and/or an executive function disorder (such as but not limited to attention deficit hyperactivity disorder (ADHD), sensory-processing disorder (SPD), mild cognitive impairment (MCI), Alzheimer's disease, multiple-sclerosis, schizophrenia, depression, or anxiety).

As used herein, the term "includes" means includes but is not limited to, the term "including" means including but not limited to. The term "based on" means based at least in part on.

The instant disclosure is also directed to example systems that include platform products and cognitive and emotional training platforms that are configured for coupling with one or more physiological or monitoring component and/or cognitive testing component. In some examples, the systems include platform products and cognitive platforms that are integrated with the one or more other physiological or monitoring component and/or cognitive testing component. In other examples, the systems include platform products and cognitive platforms that are separately housed from and configured for communicating with the one or more physiological or monitoring component and/or cognitive testing component, to receive data indicative of measurements made using such one or more components.

In any example herein, the one or more physiological components can include any means of measuring physical characteristics of the body and nervous system, including electrical activity, heart rate, blood flow, and oxygenation levels, to provide the data or physiological input. This can include camera-based heart rate detection, measurement of galvanic skin response, blood pressure measurement, electroencephalogram, electrocardiogram, magnetic resonance imaging, near-infrared spectroscopy, ultrasound, and/or pupil dilation measures, to provide the physiological input.

Other examples of physiological measurements to provide physiological input include, but are not limited to, the measurement of body temperature, heart or other cardiac-related functioning using an electrocardiograph (ECG), electrical activity using an electroencephalogram (EEG), event-related potentials (ERPs), functional magnetic resonance imaging (fMRI), blood pressure, electrical potential at a portion of the skin, galvanic skin response (GSR), magnetoencephalogram (MEG), eye-tracking device or other optical detection device including processing units programmed to determine degree of pupillary dilation, functional near-infrared spectroscopy (fNIRS), and/or a positron emission tomography (PET) scanner. An EEG-fMRI or MEG-fMRI measurement allows for simultaneous acquisition of electrophysiology (EEG/MEG) data and hemodynamic (fMRI) data.

The fMRI also can be used to provide provides measurement data indicative of neuronal activation, based on the difference in magnetic properties of oxygenated versus de-oxygenated blood supply to the brain. The fMRI can provide an indirect measure of neuronal activity by measuring regional changes in blood supply, based on a positive correlation between neuronal activity and brain metabolism.

A PET scanner can be used to perform functional imaging to observe metabolic processes and other physiological measures of the body through detection of gamma rays emitted indirectly by a positron-emitting radionuclide (a tracer). The tracer can be introduced into the user's body using a biologically active molecule. Indicators of the metabolic processes and other physiological measures of the body can be derived from the scans, including from computer reconstruction of two- and three-dimensional images of from data of tracer concentration from the scans. The data can include measures of the tracer concentration and/or the PET images (such as two- or three-dimensional images).

As used herein, the term "computerized stimuli or interaction" or "CSI" refers to a computerized element that is presented to a user to facilitate the user's interaction with a stimulus or other interaction. As non-limiting examples, the computing device can be configured to present auditory stimulus or initiate other auditory-based interaction with the user, and/or to present vibrational stimuli or initiate other vibrational based interaction with the user, and/or to present tactile stimuli or initiate other tactile based interaction with the user, and/or to present visual stimuli, image, icon, or initiate other visual based interaction with the user.

Any task according to the principles herein can be presented to a user via a computing device, actuating component, or other device that is used to implement one or more stimuli or other interactive element. For example, the task can be presented to a user by rendering a graphical user interface to present the computerized stimuli or interaction (CSI) or other interactive elements. In other examples, the task can be presented to a user as auditory, tactile, or vibrational computerized elements (including CSIs) using an actuating component. Description of use of (and analysis of data from) one or more CSIs in the various examples herein also encompasses use of (and analysis of data from) tasks comprising the one or more CSIs in those examples.

In an example, the affective modification or emotional recognition training platform and/or platform product can be configured as a processor-implemented system, method or apparatus that includes and at least one processing unit. In an example, the at least one processing unit can be programmed to render at least one graphical user interface to present the computerized stimuli or interaction (CSI) or other interactive elements to the user for interaction. In other examples, the at least one processing unit can be programmed to cause an actuating component of the platform product to effect auditory, tactile, or vibrational computerized elements (including CSIs) to affect the stimulus or other interaction with the user. The at least one processing unit can be programmed to cause a component of the program product to receive data indicative of at least one user response based on the user interaction with the CSI or other interactive element, including responses provided using the input device. In an example where at least one graphical user interface is rendered to present the computerized stimuli or interaction (CSI) or other interactive elements to the user, the at least one processing unit can be programmed to cause graphical user interface to receive the data indicative of at least one user response.

In other examples, the platform product can be configured as a processor-implemented system, method or apparatus that includes a display component, an input device, and the at least one processing unit. The at least one processing unit can be programmed to render at least one graphical user interface, for display at the display component, to present the computerized stimuli or interaction (CSI) or other interactive elements to the user for interaction. In other examples, the at least one processing unit can be programmed to cause an actuating component of the platform product to effect auditory, tactile, or vibrational computerized elements (including CSIs) to affect the stimulus or other interaction with the user.

Non-limiting examples of an input device include a touchscreen, or other pressure-sensitive or touch-sensitive surface, a motion sensor, a position sensor, a pressure sensor, joystick, exercise equipment, and/or an image capture device (such as but not limited to a camera).

According to the principles herein, the term "cognition" or "cognitive" refers to the mental action or process of acquiring knowledge and understanding through thought, experience, and the senses. This includes, but is not limited to, psychological concepts/domains such as, executive function, memory, perception, attention, emotion, motor control, and interference processing. An example computer-implemented device according to the principles herein can be configured to collect data indicative of user interaction with a platform product, and to compute metrics that quantify user performance. The quantifiers of user performance can be used to provide measures of cognition (for cognitive assessment) or to provide measures of status or progress of a cognitive treatment.

According to the principles herein, the term "treatment" or "treat" refers to any manipulation of CSI in a platform product that results in a measurable improvement of a user, such as but not limited to improvements related to cognition, a user's mood, emotional state, and/or level of engagement or attention to the cognitive, emotional mimicry empathy recognition and training platform. The degree or level of improvement can be quantified based on user cognitive bias or affective state measures as describe herein. In an example, the term "treatment" may also refer to a therapy.

According to the principles herein, the term "affect" refers to a concept used in psychology to describe the experience of feeling or emotion. The word "affect" also refers sometimes to affect display, which is a facial, vocal, or gestural behavior that serves as an indicator of affect.

According to the principles herein, the term "valence" refers the intrinsic attractiveness/"good"-ness (positive valence) or averseness/"bad"-ness (negative valence) of an event, object, or situation. The term also characterizes and categorizes specific emotions. For example, emotions referred to as "negative," such as anger and fear, have negative valence. Joy has positive valence. Positively valenced emotions are evoked by positively valenced events, objects, or situations. The term is also used to describe the hedonic tone of feelings, affect, certain behaviors (for example, approach and avoidance), goal attainment or nonattainment, and conformity with, or violation of, social norms.

As described hereinabove, the example systems, methods, and apparatus according to the principles herein can be implemented, using at least one processing unit of a programmed computing device, to provide the affective modification or emotional recognition training platform and/or platform product (herein after "Emotional Expression Training platform"). FIG. 1 shows an example apparatus 100 according to the principles herein that can be used to implement the Emotional Expression Training platform and/or platform product including the system and methods described within the present disclosure. The example apparatus 100 includes at least one memory 102 and at least one processing unit 104. The at least one processing unit 104 is communicatively coupled to the at least one memory 102.

Example memory 102 can include, but is not limited to, hardware memory, non-transitory tangible media, magnetic storage disks, optical disks, flash drives, computational device memory, random access memory, such as but not limited to DRAM, SRAM, EDO RAM, any other type of memory, or combinations thereof. Example processing unit 104 can include, but is not limited to, a microchip, a processor, a microprocessor, a special purpose processor, an application specific integrated circuit, a microcontroller, a field programmable gate array, any other suitable processor, or combinations thereof.

The at least one memory 102 is configured to store processor-executable instructions 106 and a computing component 108. In a non-limiting example, the computing component 108 can be used to analyze the cData and/or nData received from the cognitive platform and/or platform product coupled with the one or more physiological or monitoring components and/or cognitive testing components as described herein. As shown in FIG. 1, the memory 102 also can be used to store data 110, including but not limited to, facial image data from a camera, the physiological data (pData) 112 (including computational measurement data from measurement(s) using one or more physiological or monitoring components and/or cognitive testing components) and/or data indicative of the response of an individual to the one or more tasks, including responses to tasks rendered at a graphical user interface of the apparatus 100 and/or tasks generated using an auditory, tactile, or vibrational signal from an actuating component coupled to or integral with the apparatus 100. The data 110 can be received from one or more physiological or monitoring components and/or cognitive testing components that are coupled to or integral with the apparatus 100.

In a non-limiting example, the at least one processing unit 104 executes the processor-executable instructions 106 stored in the memory 102 at least to analyze digital image data from a camera and/or pData received from the Emotional Expression Training platform and/or platform product coupled with the one or more physiological or monitoring components and/or cognitive testing components as described herein, using the computing component 108. The at least one processing unit 104 also can be configured to execute processor-executable instructions 106 stored in the memory 102 to generate computation results indicative of a user valence or intensity/arousal or affect. The at least one processing unit 104 also executes processor-executable instructions 106 to control a transmission unit to transmit values indicative of the analysis received from the Emotional Expression Training platform and/or platform product coupled with the one or more physiological or monitoring components and/or cognitive testing components as described herein, and/or controls the memory 102 to store values indicative of the analysis.

Figure 2:
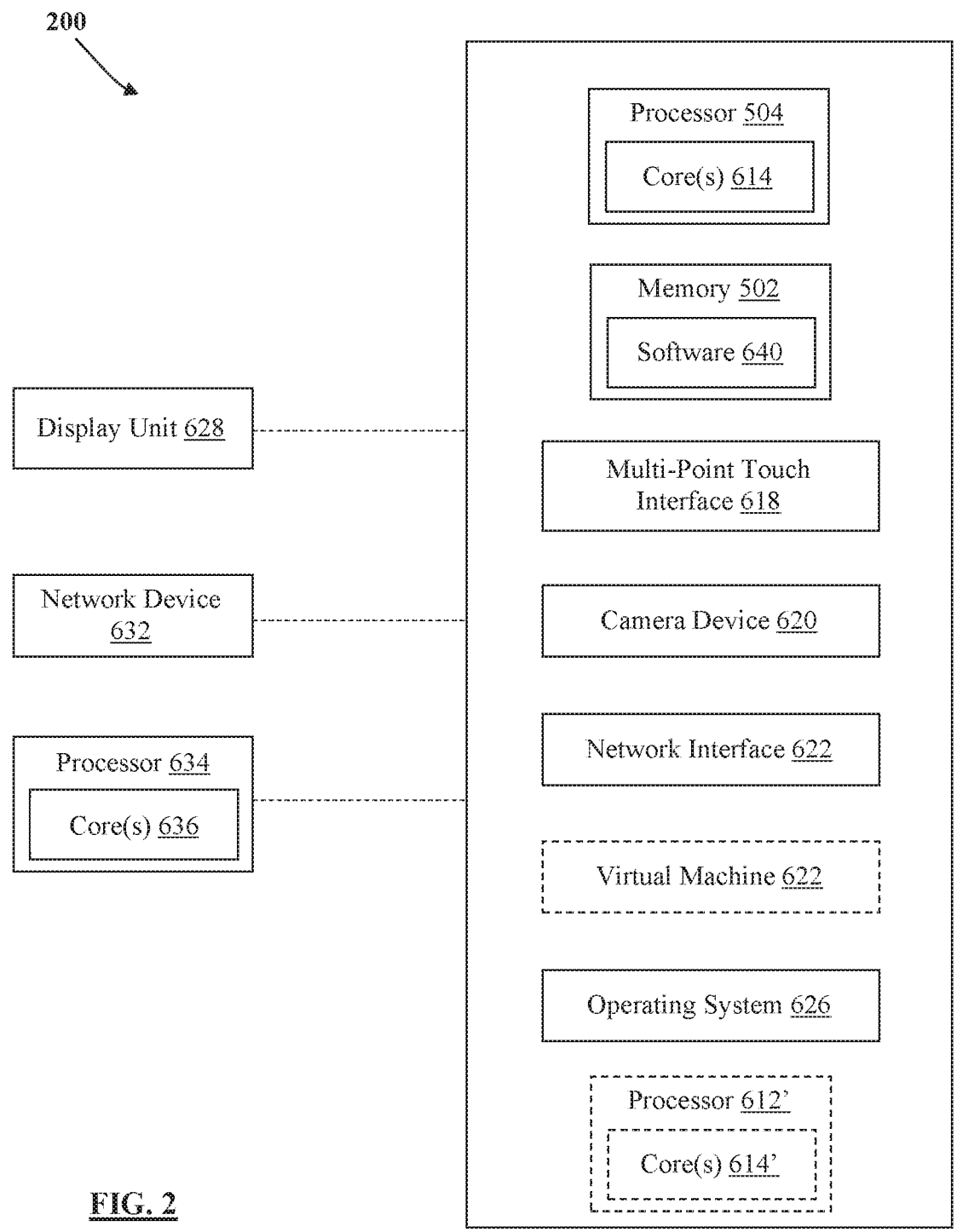
FIG. 2 is a functional block diagram of system architecture through which one or more aspects of the present disclosure may be implemented.

FIG. 2 is a block diagram of an example computing device 200 that can be used as a computing component according to the principles herein. In any example herein, computing device 200 can be configured as a console that receives user input to implement the computing component. For clarity, FIG. 2 also refers back to and provides greater detail regarding various elements of the example system of FIG. 1. The computing device 200 can include one or more non-transitory computer-readable media for storing one or more computer-executable instructions or software for implementing examples. The non-transitory computer-readable media can include, but are not limited to, one or more types of hardware memory, non-transitory tangible media (for example, one or more magnetic storage disks, one or more optical disks, one or more flash drives), and the like. For example, memory 502 included in the computing device 200 can store computer-readable and computer-executable instructions or software for performing the operations disclosed herein. For example, the memory 502 can store a software application 640 which is configured to perform various combinations of the disclosed operations (e.g., analyze platform and/or platform product measurement data and response data, facial recognition, emotion recognition or performing a computation). The computing device 200 also includes configurable and/or programmable processor 504 and an associated core 614, and optionally, one or more additional configurable and/or programmable processing devices, e.g., processor(s) 612' and associated core(s) 614' (for example, in the case of computational devices having multiple processors/cores), for executing computer-readable and computer-executable instructions or software stored in the memory 502 and other programs for controlling system hardware. Processor 504 and processor(s) 612' can each be a single core processor or multiple core (614 and 614') processor.

Virtualization can be employed in the computing device 200 so that infrastructure and resources in the console can be shared dynamically. A virtual machine 624 can be provided to handle a process running on multiple processors so that the process appears to be using only one computing resource rather than multiple computing resources. Multiple virtual machines can also be used with one processor.

Memory 502 can include a computational device memory or random-access memory, such as but not limited to DRAM, SRAM, EDO RAM, and the like. Memory 502 can include a non-volatile memory, such as but not limited to a hard-disk or flash memory. Memory 502 can include other types of memory as well, or combinations thereof.

In a non-limiting example, the memory 502 and at least one processing unit 504 can be components of a peripheral device, such as but not limited to a dongle (including an adapter) or other peripheral hardware. The example peripheral device can be programmed to communicate with or otherwise coupled to a primary computing device, to provide the functionality of any of the example cognitive platform and/or platform product, apply an example classifier model, and implement any of the example analyses (including the associated computations) described herein. In some examples, the peripheral device can be programmed to directly communicate with or otherwise couple to the primary computing device (such as but not limited to via a USB or HDMI input), or indirectly via a cable (including a coaxial cable), copper wire (including, but not limited to, PSTN, ISDN, and DSL), optical fiber, or other connector or adapter. In another example, the peripheral device can be programmed to communicate wirelessly (such as but not limited to Wi-Fi or Bluetooth®) with primary computing device. The example primary computing device can be a smartphone (such as but not limited to an iPhone®, a BlackBerry®, or an Android™-based smartphone), a television, a workstation, a desktop computer, a laptop, a tablet, a slate, an electronic-reader (e-reader), a digital assistant, or other electronic reader or hand-held, portable, or wearable computing device, or any other equivalent device, an Xbox®, a Wii®, or other equivalent form of computing device.

A user can interact with the computing device 200 through a visual display unit 628, such as a computer monitor, which can display one or more user interfaces 630 that can be provided in accordance with example systems and methods. The computing device 200 can include other I/O devices for receiving input from a user, for example, a keyboard or any suitable multi-point touch interface 618, a camera device 620, a mouse, a microphone or other sound recording device, an accelerometer, a gyroscope, a sensor for tactile, vibrational, or auditory signal, and/or at least one actuator. The keyboard 618 and the camera device 620 can be coupled to the visual display unit 628. The computing device 200 can include other suitable conventional I/O peripherals.

The computing device 200 can also include one or more storage devices 634 (including a single core processor or multiple core processor 636), such as a hard-drive, CD-ROM, or other computer readable media, for storing data and computer-readable instructions and/or software that perform operations disclosed herein. Example storage device 634 (including a single core processor or multiple core processor 636) can also store one or more databases for storing any suitable information required to implement example systems and methods. The databases can be updated manually or automatically at any suitable time to add, delete, and/or update one or more items in the databases.

The computing device 200 can include a network interface 622 configured to interface via one or more network devices 632 with one or more networks, for example, Local Area Network (LAN), metropolitan area network (MAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 622 can include a built-in network adapter, network interface card, PCMCIA network card, card bus network adapter, wireless network adapter, USB network adapter, modem or any other device suitable for interfacing the computing device 200 to any type of network capable of communication and performing the operations described herein. Moreover, the computing device 200 can be any computational device, such as a smartphone (such as but not limited to an iPhone®, a BlackBerry®, or an Android™-based smartphone), a television, a workstation, a desktop computer, a server, a laptop, a tablet, a slate, an electronic-reader (e-reader), a digital assistant, or other electronic reader or hand-held, portable, or wearable computing device, or any other equivalent device, an Xbox®, a Wii®, or other equivalent form of computing or telecommunications device that is capable of communication and that has or can be coupled to sufficient processor power and memory capacity to perform the operations described herein. The one or more network devices 632 may communicate using different types of protocols, such as but not limited to WAP (Wireless Application Protocol), TCP/IP (Transmission Control Protocol/Internet Protocol), NetBEUI (NetBIOS Extended User Interface), or IPX/SPX (Internetwork Packet Exchange/Sequenced Packet Exchange).

The computing device 200 can run any operating system 626, such as any of the versions of the Microsoft® Windows® operating systems, iOS® operating system, Android™ operating system, the different releases of the Unix and Linux operating systems, any version of the MacOS® for Macintosh computers, any embedded operating system, any real-time operating system, any open source operating system, any proprietary operating system, or any other operating system capable of running on the console and performing the operations described herein. In some examples, the operating system 626 can be run in native mode or emulated mode. In an example, the operating system 626 can be run on one or more cloud machine instances.

Figure 3:
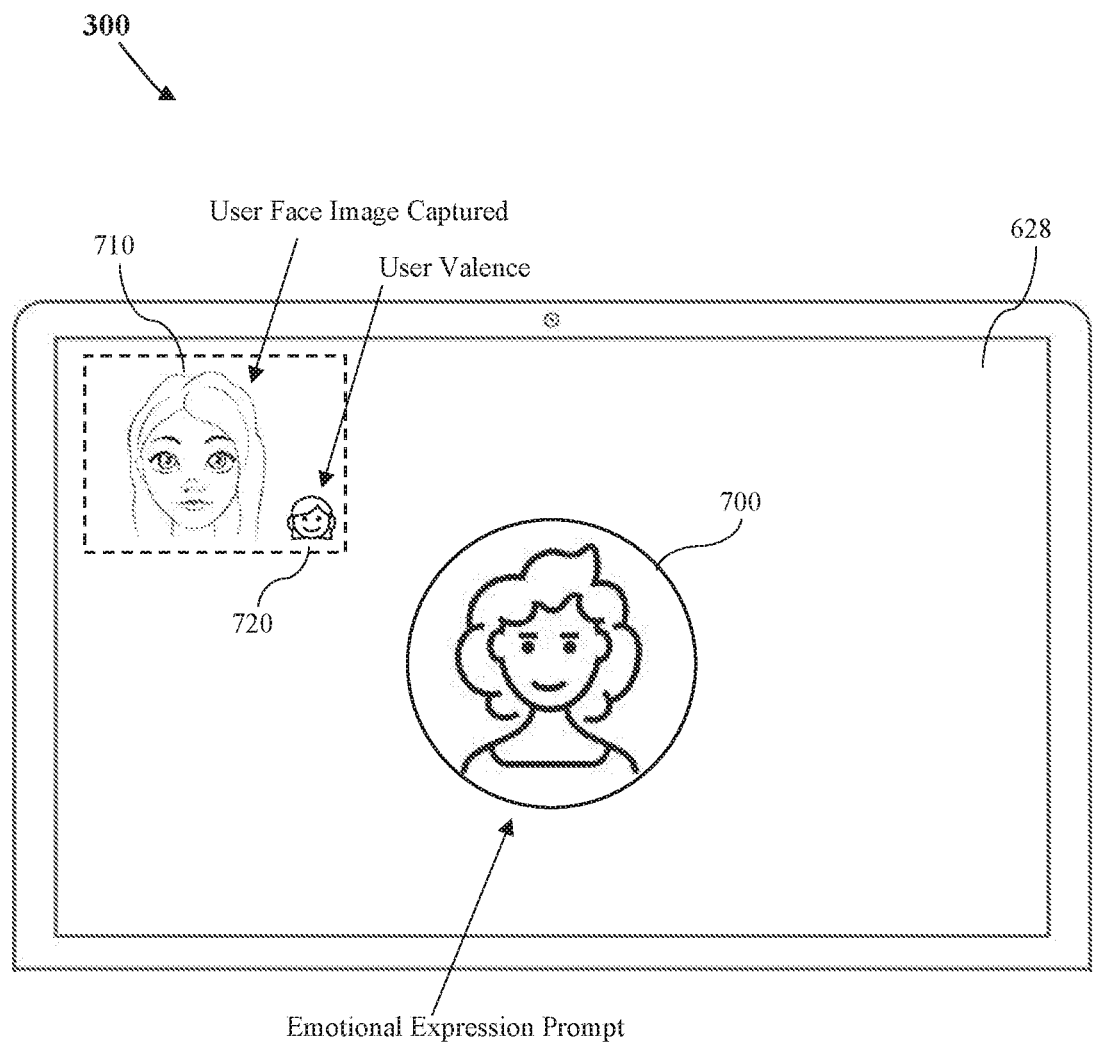
FIG. 3 diagram of depicting the relationship between a facial expression prompt, image capture, and user valence, in accordance with an embodiment.

The storage devices 634 of the present disclosure comprises instructions for number of operations for the Emotional Expression Training platform. In FIG. 3 one or more instructions enable computing device 200 to render on display unit 628 a computer stimulus 700, comprising an emotional expression prompt, image, icon, or the like. Computing device 200, receives preferably in real-time, one or more digital image 710 of a facial expression of a user in response to the computerized stimuli or interaction 700. Computing device 200 the processes the digital image 710 to determine a valence input 720 corresponding to the facial expression. Computing 200 then comparing the valence input 720 to a predetermined intensity range associated with the emotional expression prompt 700 stored within one or more storage devices 634. In an alternative embodiment, valence input 720 comprises an intensity or arousal input. Computing device 200 then executes instructions for determining a measure of concordance between the facial expression 710 of the user and the emotional expression prompt 700 or one or more CSIs. In various embodiments, the Emotional Expression platform or platform-product enables the detection and tracking of a person's ability to mimic one or more facial expressions. In one embodiment, one or more operations for detection and tracking enable the screening of one or more specific psychopathologies or diseases. In various embodiments, training of a user by capturing one or more images 710 to replicate emotional expression prompt 700 with increased efficiency may offer an effective treatment or intervention. In various embodiments, image 710 is a live video feed of a user's face and valence 720 indicating one or more detected expression. A user is able to quickly learn how others may read their facial expressions immediately. The user is then trained to mimic an expression in response to emotional expression prompt 700 and may receive real-time feedback on the accuracy in replicating or mimicking an expression.

Figure 4:
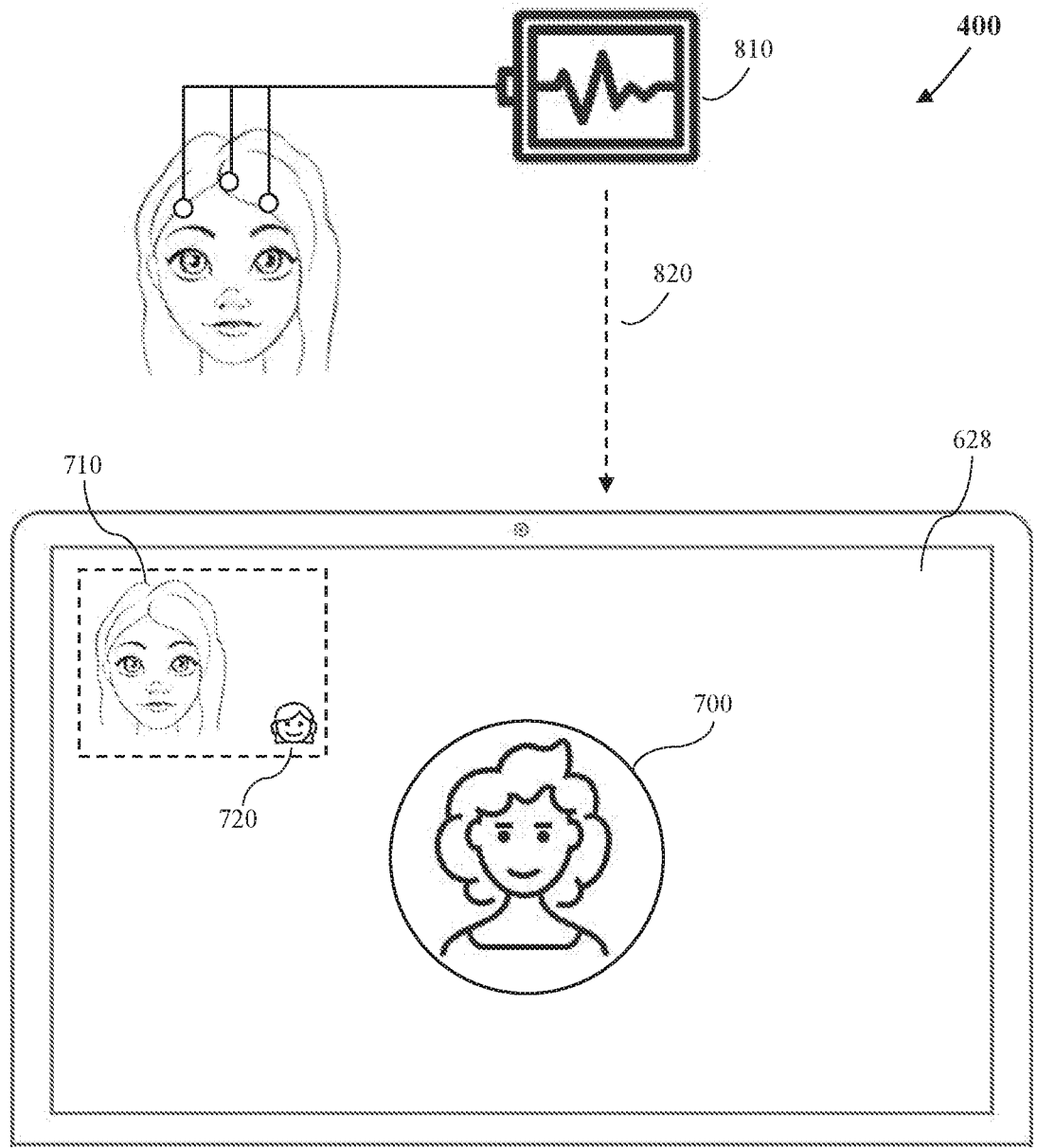
FIG. 4 is a depiction of the Emotional Expression Training platform incorporating a physiological sensor to identify, target, or modify on or more specific emotion, in accordance with an embodiment.

FIG. 4 depicts an Emotional Expression Training platform system with the incorporation of a physiological sensor to identify, target, or modify one or more specific emotion. In an exemplary implementation, physiological sensor 810 enables the measurement and collection of one or more physiological sensor input 820 in response to one or more emotional expression prompt 700 of FIG. 3. In various embodiments, computing device 200 of FIG. 2 executes one or more operating instructions from storage devices 634 of FIG. 2 to determine a measure of a cognitive bias or an affective state of the user from one or more captured images 710 of FIG. 3 according to the measure of concordance between the facial expression of the user and the emotional expression prompt 700 of FIG. 3. In a non-limiting example implementation, the EEG 810 can be a low-cost EEG for medical treatment validation and/or personalized treatment or intervention. The low-cost EEG device can be easier to use and has the potential to vastly improve the accuracy and the validity of medical applications. In this example, the platform product may be configured as an integrated device including the EEG component coupled with the Emotional Expression Training platform, or as a cognitive and/or affective platform that is separate from, but configured for coupling with the EEG component.

In a non-limiting example use for training validation, the user interacts with the Emotional Expression Training platform, and the EEG is used to perform physiological measurements of the user. Any change in EEG measurements data (such as brainwaves) are monitored based on the actions of the user in interacting with the cognitive platform. The physiological input 820 from the measurements using the EEG (such as brainwaves) can be collected and analyzed to detect changes in the EEG measurements. This analysis can be used to determine the types of response from the user such as valence, affect, intensity, or the like.

In a non-limiting example use for personalized medicine, the physiological input 820 from the EEG measurements be used to identify level and/or changes in cognition or emotion or empathy that indicate that the Emotional Expression Training platform treatment is having the desired effect (including to determine the type of tasks and/or CSIs 700 that works for a given user). The analysis can be used to determine whether the Emotional Expression Training platform should be caused to provide tasks and/or CSIs to enforce or diminish these user results that the EEG is detecting, by adjusting user experience in the application.

In a non-limiting example implementation, physiological measurements from 810 are made using the Emotional Expression Training platform that is configured for coupling with a fMRI, for use for medical application validation and personalized medicine, treatment, or intervention. Consumer-level fMRI devices may be used to improve the accuracy and the validity of medical applications by tracking and detecting changes in brain part stimulation.

In a non-limiting example, fMRI measurements can be used to provide measurement data of the cortical thickness and other similar measurement data. In a non-limiting example use for treatment validation, the user interacts with a cognitive platform, and the fMRI is used to measure physiological data. The user is expected to have stimulation of a particular brain part or combination of brain parts based on the actions of the user while interacting with the cognitive platform. In this example, the platform product may be configured as an integrated device including the fMRI component coupled with the cognitive platform, or as a cognitive platform that is separate from, but configured for coupling with the fMRI component. Using the application with the fMRI, measurement can be made of the stimulation of portions of the user brain, and analysis can be performed to detect changes to determining whether the user is exhibiting the desired responses.

In a non-limiting example use for personalized treatment or intervention, the fMRI can be used to collect measurement data to be used to identify the progress of the user in interacting platform. The analysis can be used to determine whether the Emotional Expression Training platform should be caused to provide tasks and/or CSIs to enforce or diminish these user results that the fMRI is detecting, by adjusting users experience in the application.

In any example herein, the adjustment(s) or modification(s) to, or presentments of, the type of tasks, notifications, and/or CSIs can be made in real-time. In various embodiments physiology measurements (e.g., EEG, fMRI, etc.) and/or facial recognition technology to detect one or more emotion with accuracy and specificity. In various embodiments, one or more cognition screening instruments (CSIs) are adapted to further promote one or more targeted emotion.

Figure 5:
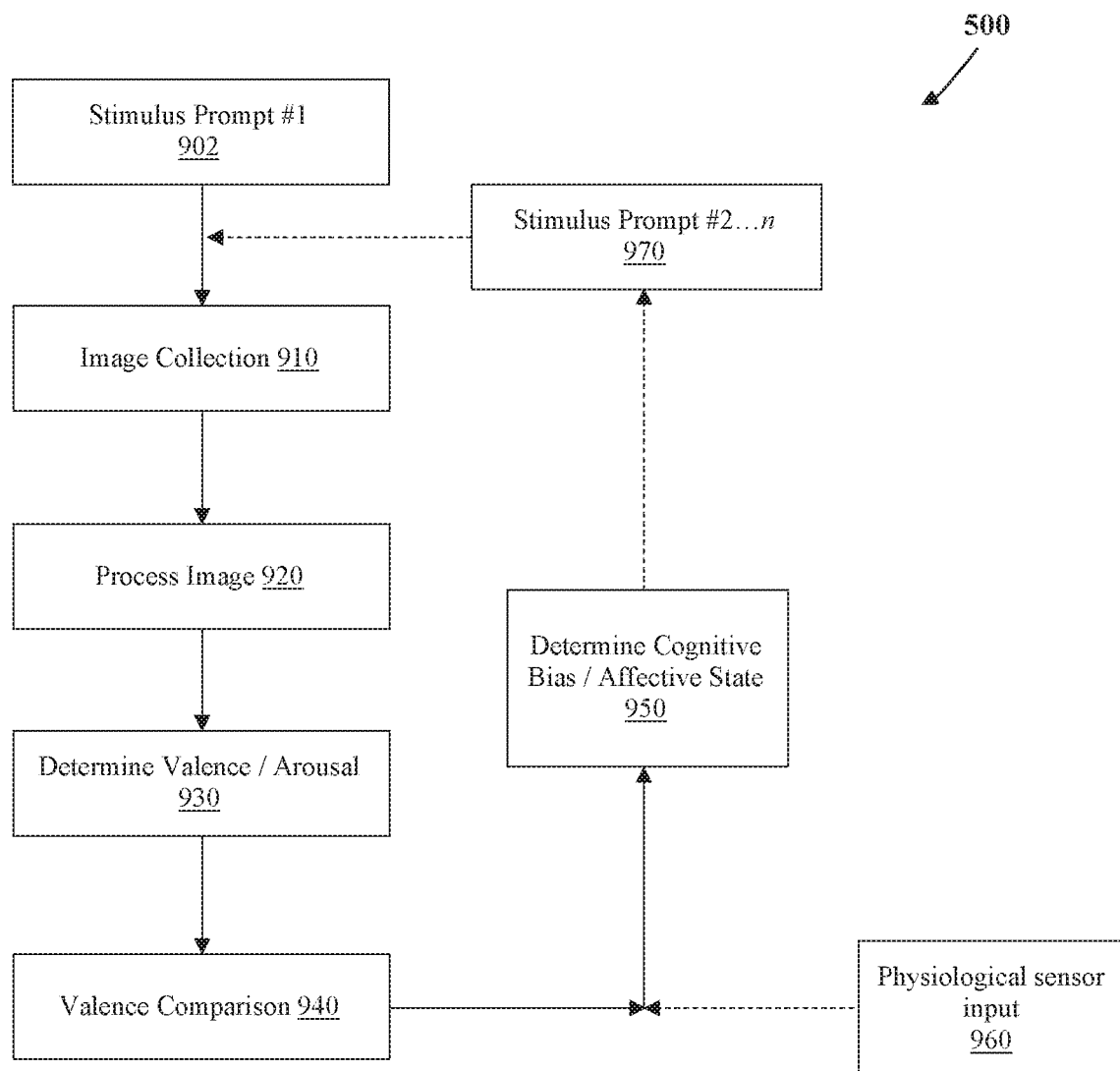
FIG. 5 is a process flow diagram of the computer-implemented method for targeting an emotion associated with a cognitive bias, in accordance with an embodiment.

Referring now to FIG. 5, a process flow diagram 500 of the computer-implemented method for targeting emotion associated with a cognitive bias is disclosed, according to various embodiments. In various embodiments, the computer-implemented method comprises facial image processing, the method further comprising computing device 200 of FIG. 2 having a user interface or display unit 628 configure to display an instance of an emotional expression prompt 700 of FIG. 3. In an alternative embodiment, the instance of emotional expression prompt 700 of FIG. 3 is a computerized interaction. In various embodiments, the computer-implemented method comprises prompting (Step 902) a user with a stimuli and receiving (Step 910) one or more digital image 710 of FIG. 3, via at least one camera device 620 of FIG. 2, of a facial expression of a user, in response to the computerized stimuli or interaction 700 of FIG. 3. In various embodiments, the method comprises steps for processing (Step 920) said digital image to determine (Step 930) one or more user valence 720 of FIG. 3 and/or one or intensity or arousal input corresponding to a facial expression. In various embodiments, the method comprises steps for comparing (Step 940) the valence and/or intensity or arousal input to a predetermined valence or intensity value range associated with a facial expression image, icon, or prompt (e.g., 700 of FIG. 3), and determining a measure of concordance between the user's facial expression and the facial expression image, icon, or prompt. In various embodiments, the method comprises steps for determining (Step 950) a measure of a user's cognitive bias or an affective state. In various embodiments, the method comprises steps for measuring (Step 960) with at least one physiology measurement (e.g., EEG, fMRI, etc.) concomitantly with said digital image, icon, or facial expression of the user in response to the facial image, icon, or facial expression prompt. In one embodiment, one or physiological measurement enables the determination (Step 950) of an affective state of a user. In various embodiments, the method comprises steps of providing (Step 970) one or more, first, second, or subsequent instance of a computerized stimuli or interaction comprising one or more facial expression prompt, image, icon, or the like. In one embodiment, the computerized stimuli or interaction comprises a computerized cognitive-bias modification regimen. In various embodiments, the method comprises steps of modifying, with the processing device, one or more first, second, or subsequent instance of a computerized stimuli or interaction according to the cognitive bias, affective state, and/or a measure of change of the cognitive bias or affective state of a user.

Figure 6:
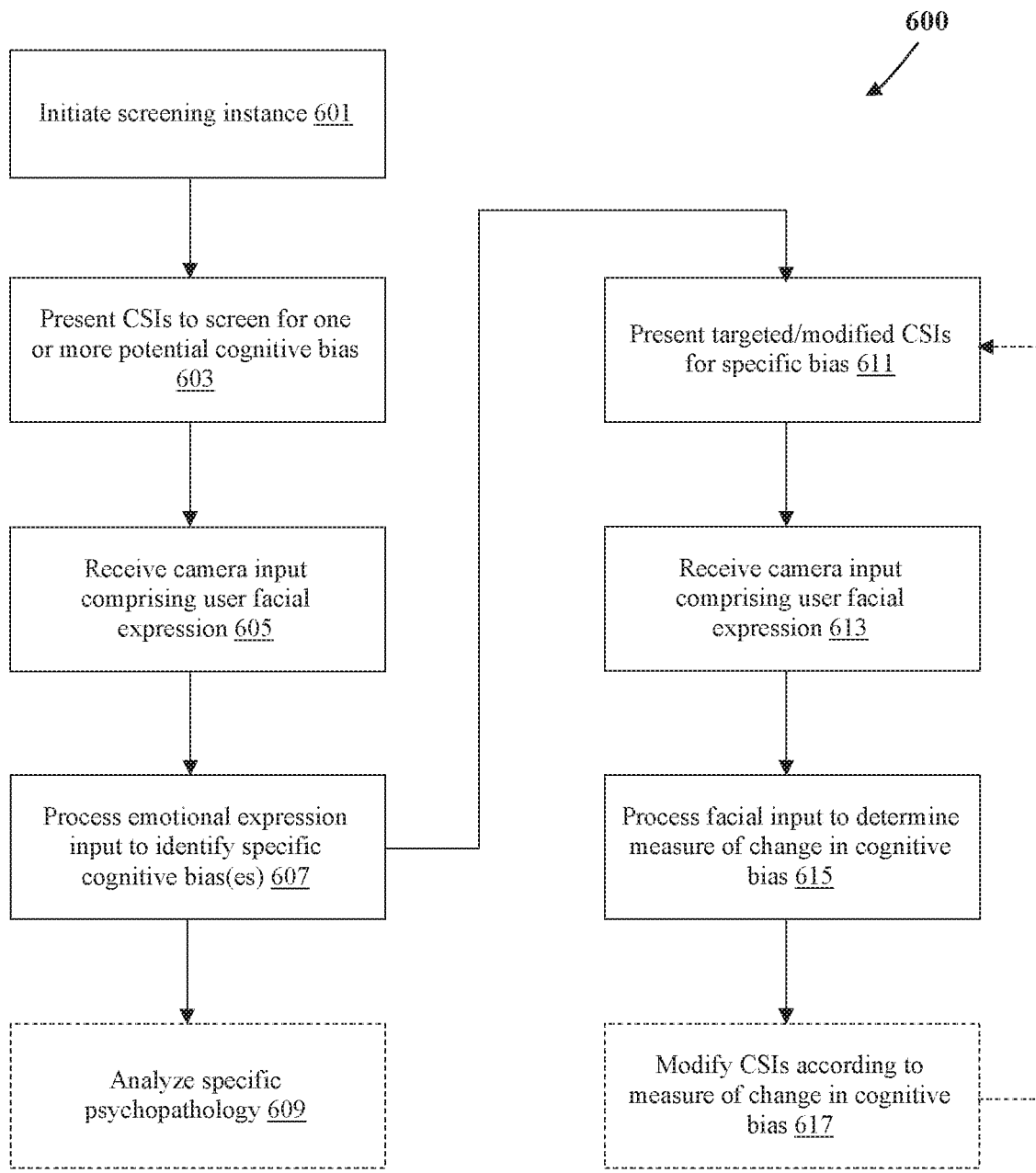
FIG. 6 is a process flow diagram of the computer-implemented method for identifying and targeting a cognitive bias associated with a specific psychopathology, in accordance with an embodiment.

FIG. 6 is a process flow diagram of a cognitive-bias modification (CBM) method 600. In accordance with various aspects of the present disclosure, method 600 may be operably configured to identify, target, and/or modify one or more cognitive biases associated one or more psychopathologies, such as depression and social anxiety. Method 600 may comprise one or more emotion recognition training tasks configured to shift a biased perception of a user of neutral or ambiguous faces, characteristic of many disorders, from negative to more positive. In accordance with certain embodiments, method 600 is embodied as a computerized CBM application. Method 600 may be commenced by initiating an instance of a CBM application 601. The CBM application may be configured to present one or more CSIs to a user via a graphical user interface 603, wherein the one or more CSIs are configured to screen for one or more potential cognitive bias in a user being associated with at least one specific psychopathology. In accordance with an embodiment, the CSIs comprise at least one emotional expression prompt. Method 600 proceeds by receiving an emotional expression input in response to the at least one emotional expression prompt comprising one or more digital images of the user's face and/or facial expression 605. Method 600 may proceed by processing the emotional expression input to quantify one or more valence and intensity/arousal data corresponding to the user's facial expression. The valence and intensity/arousal data may be further processed according to one or more parameters to determine a measure of concordance between the user's facial expression and emotional expression prompt in order to identify one or more cognitive bias in the user 607. In certain embodiments, method 600 may further comprise analyzing the valence and intensity/arousal data to screen for and identify one or more specific psychopathologies 609. Method 600 may further proceed by presenting one or more targeted or modified CSIs being configured to target one or more specific emotions in the user, wherein the one or more specific emotions are associated with the identified cognitive bias 611. The one or more targeted or modified CSIs may be presented in the same session of a CBM application and/or in subsequent sessions of the CBM application. The one or more targeted or modified CSIs may comprise one or more emotional expression prompts corresponding to one or more emotion recognition training interactions. Method 600 may further proceed, in one or more instances, by receiving a camera input comprising a digital image(s) of the user's face/facial expression in response to the one or more emotional expression prompts 613. The digital image(s) may be processed to quantify the one or more valence and intensity/arousal data corresponding to the user's facial expression. The valence and intensity/arousal data may be further processed according to one or more parameters to determine a measure of concordance between the user's facial expression and the emotional expression prompt in order assess a measure of change in the cognitive bias of the user 615. Method 600 may optionally proceed by further modifying the CSIs according to the measure of change in the cognitive bias of the user 617.

Figure 7:
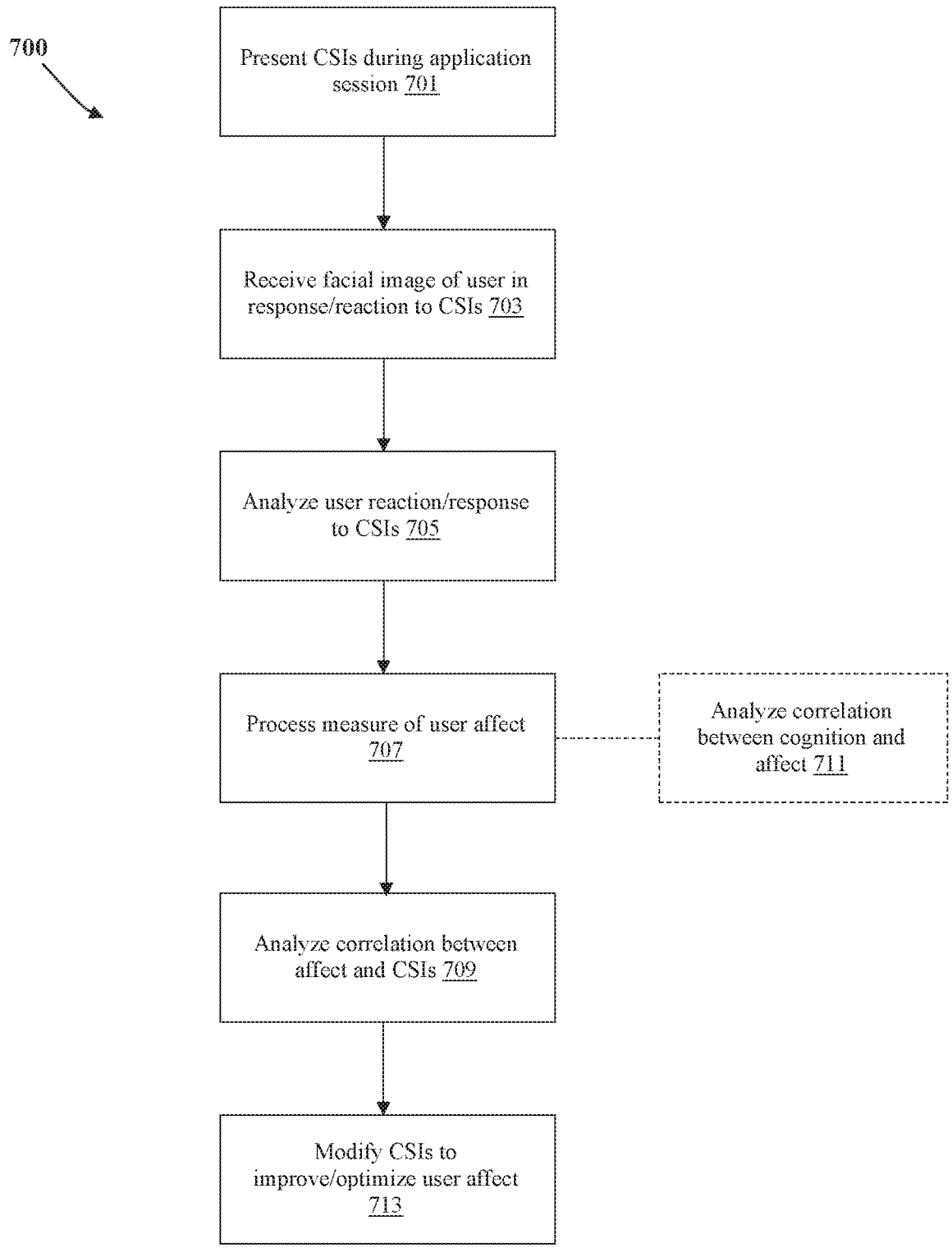
FIG. 7 is a process flow diagram of the computer-implemented method for optimizing user affect during a session of a computer application, in accordance with an embodiment.

FIG. 7 is a process flow diagram of the computer-implemented method 700 for optimizing or improving user affect during a user interaction with a software platform or application. Exemplary computerized user interactions in which embodiments of method 700 might be employed to improve or optimize user affect might include a cognitive-bias modification platform, a cognitive training platform, a mood or emotional enhancement platform, and a telemedicine or telepsychiatry platform. Exemplary computerized user interactions may further include non-medical software platforms and applications in which a user session might comprise an extended period of time, such as video games, social media platforms, and other dynamic media platforms. Method 700 may be initiated by presenting one or more CSIs to a user during a session of a software platform or application 701. In accordance with certain embodiments, the software platform or application may be communicably engaged (either directly or indirectly) with at least one digital camera configured to capture and communicate one or more real-time digital images of a user's face in response/reaction to the one or more CSIs 703. In certain embodiments wherein the CSIs comprise an emotional expression prompt, the user may intentionally respond to the one or more CSIs by providing a facial expression to the camera. In other embodiments, the camera may be configured to continuously capture one or more real-time digital images of the user's face in reaction to one or more CSIs during the session of a software platform or application. Method 700 may proceed by analyzing one or more valence and intensity/arousal characteristics of the one or more real-time digital images of a user's face in response/reaction to the one or more CSIs 705. The valence and intensity/arousal data may be further processed according to one or more static or dynamic affect parameters to determine a real-time measure/degree a user's affective state during different time points in the session of the software application or platform 707. The real-time measure/degree of user affect within the session of the software application or platform may be further analyzed to determine temporal patterns and/or correlations between the presentment of specific CSIs and the user's affective state 709. In accordance with certain embodiments wherein the software application or platform comprises a cognitive training platform, method 700 may further comprise analyzing user performance data against user affect data to determine a degree of correlation between user affective state and user cognitive performance within the cognitive training platform 711. Method 700 may further comprise modifying one or more aspects of the CSIs in response to the temporal patterns and/or correlations between the presentment of specific CSIs and the user's affective state in order to further improve or optimize a user's affective state during the session of the software application 713.

Figure 8:
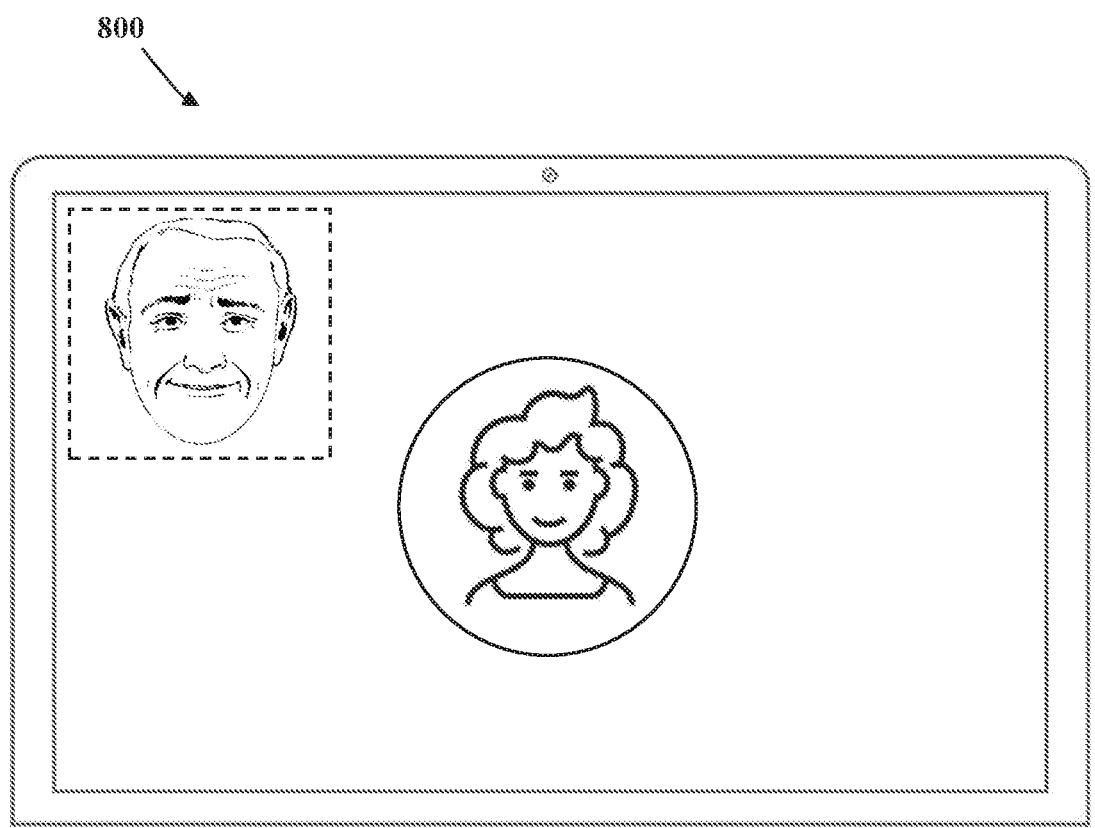
FIG. 8 is a graphical user interface illustration of a CSI comprising a facial mimicry prompt, in accordance with an embodiment.

FIGS. 8-12 provide a plurality of illustrative examples of emotional expression prompts comprising one or more CSIs that may be incorporated into various aspects of the methods and systems embodied by the present disclosure. FIG. 8 is a graphical illustration of a CSI comprising a facial mimicry prompt 800. In accordance with an embodiment, a facial mimicry prompt 800 comprises presenting an image or representation of a face to a user in response to which the user is prompted to mimic the facial expression of the face. Certain systems and methods of the present disclosure may comprise presenting one or more instances of CSIs comprising facial mimicry prompt 800 within an Emotional Expression Training platform or platform-product.

Figure 9:
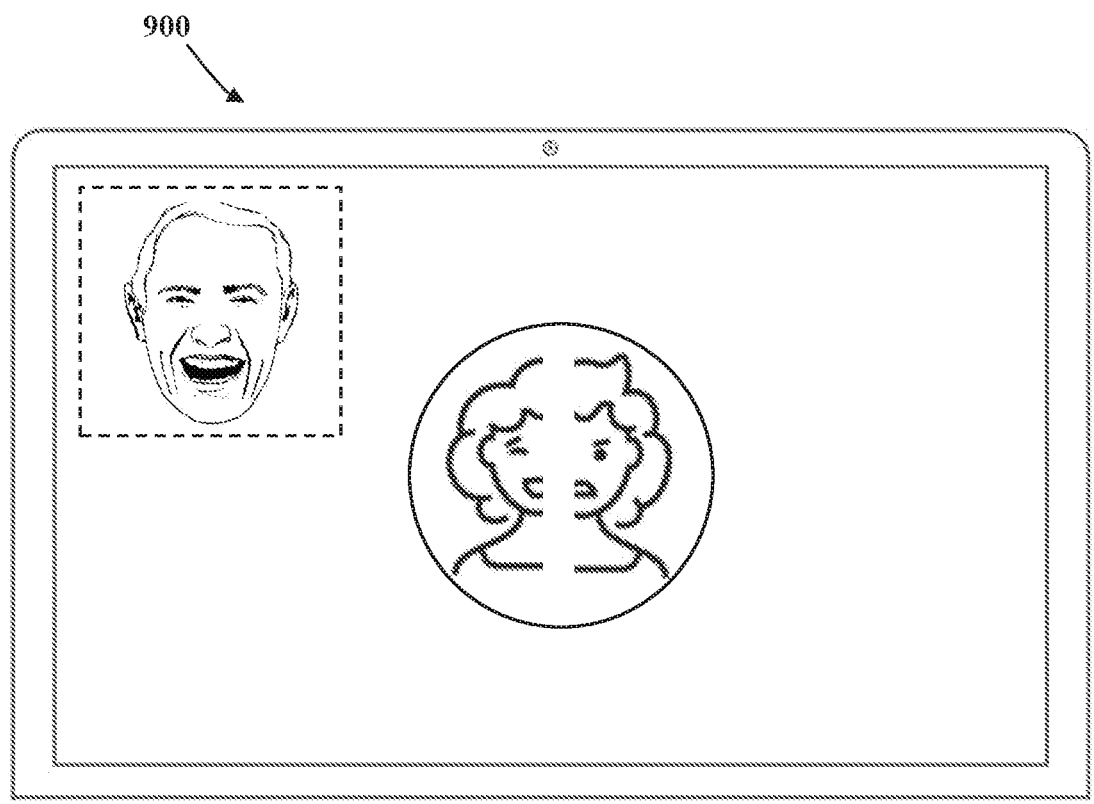
FIG. 9 is a graphical user interface illustration of a CSI comprising a facial mimicry prompt with a partial expression conflict, in accordance with an embodiment.

FIG. 9 is a graphical user interface illustration of a CSI comprising a facial mimicry prompt with a partial expression conflict 900. In accordance with an embodiment, a facial mimicry prompt with a partial expression conflict 900 comprises presenting an image or representation of a composite face comprising two or more conflicting expressions to a user. The user is prompted to distinguish between the two or more conflicting expressions and is prompted to ignore one or more non-target expressions in the composite image and mimic the other. Certain systems and methods of the present disclosure may comprise presenting one or more instances of CSIs comprising facial mimicry prompt with a partial expression conflict 900 within an Emotional Expression Training platform or platform-product.

Figure 10:
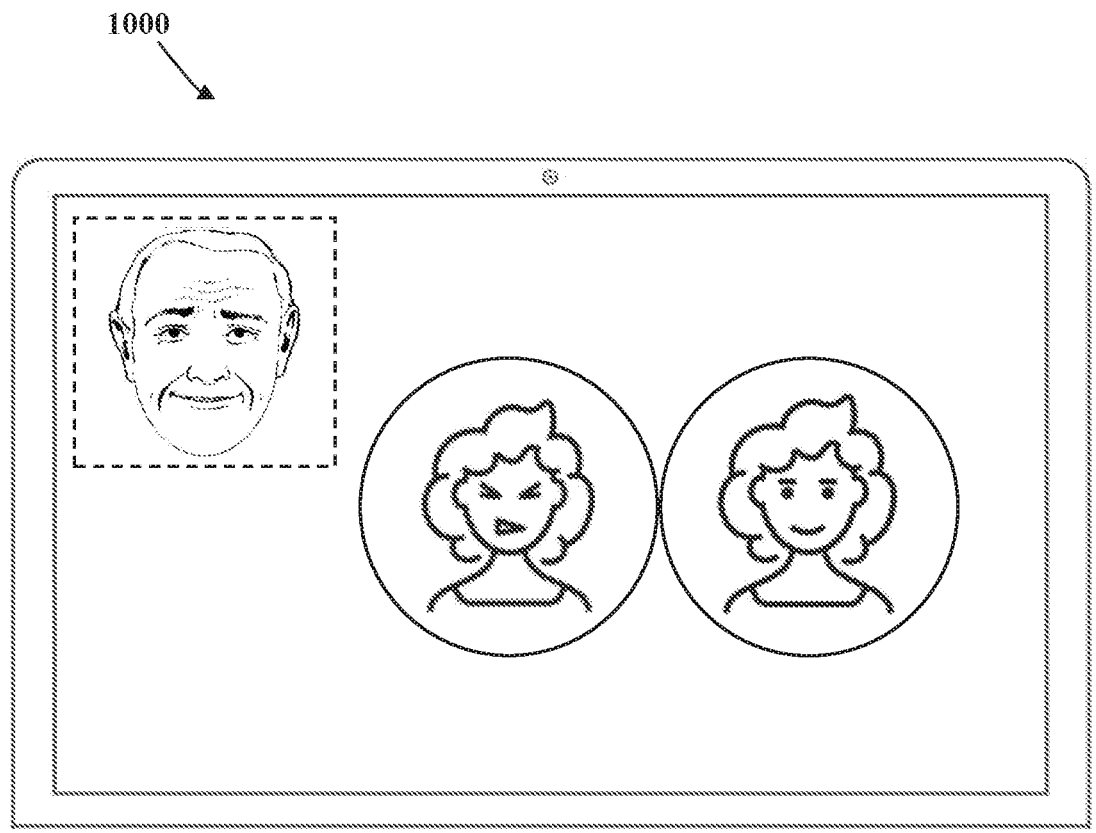
FIG. 10 is a graphical user interface illustration of a CSI comprising a facial mimicry prompt with a multiple expression conflict, in accordance with an embodiment.

FIG. 10 is a graphical user interface illustration of a CSI comprising a facial mimicry prompt with a multiple expression conflict 1000. In accordance with an embodiment, a facial mimicry prompt with a multiple expression conflict 1000 comprises presenting to a user an image of a first face having a first expression and an image of a second face having a second and conflicting expression to that of the first face. The user is prompted to distinguish between the two conflicting expressions and is prompted to ignore one of the expressions and mimic the other. Certain systems and methods of the present disclosure may comprise presenting one or more instances of CSIs comprising facial mimicry prompt with a multiple expression conflict 1000 within an Emotional Expression Training platform or platform-product.

Figure 11:
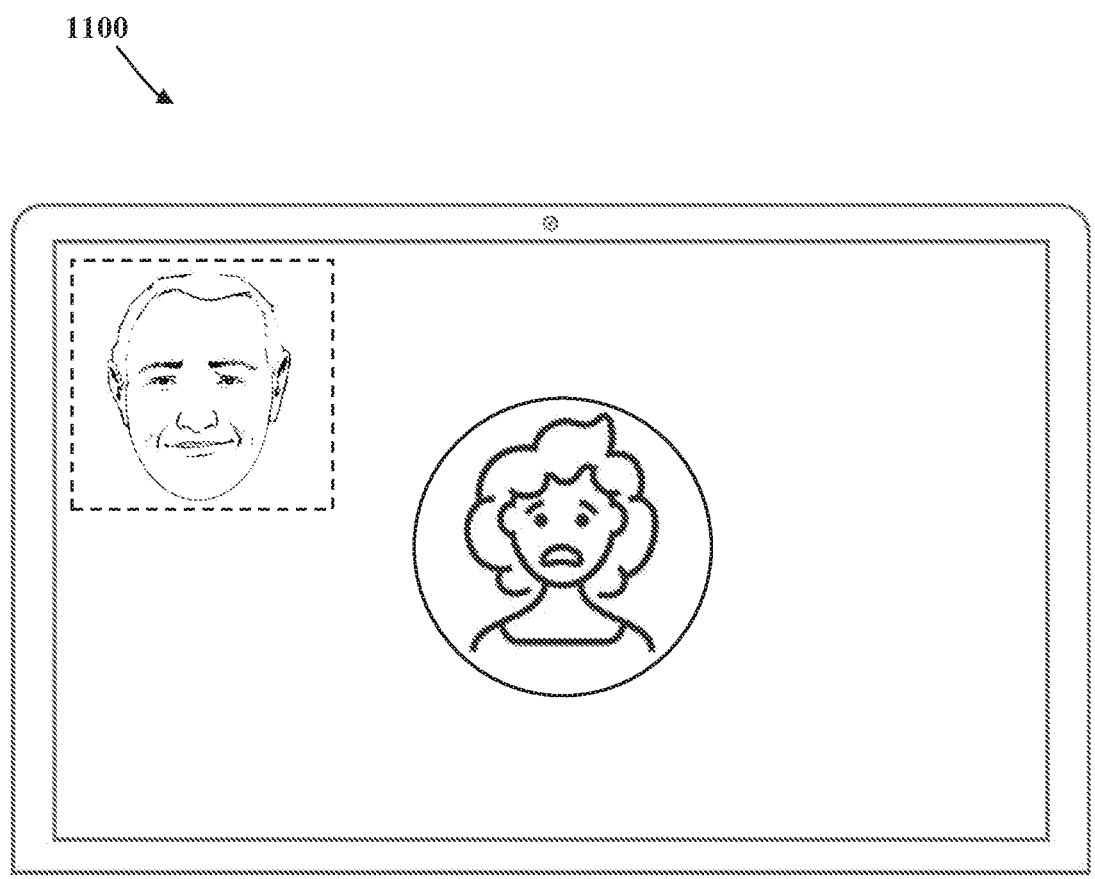
FIG. 11 is a graphical user interface illustration of a CSI comprising an emotional stimulus with an emotional suppression instruction, in accordance with an embodiment.

FIG. 11 is a graphical user interface illustration of a CSI comprising an emotional stimulus with an emotional suppression instruction 1100. In accordance with an embodiment, an emotional stimulus with an emotional suppression instruction 1100 comprises presenting to a user an image having subject matter intended to invoke an emotional reaction in the user. The image may consist of an image of a face with an emotional expression, or the image may consist of an image selected from the International Affective Picture System (IAPS) (or other subject matter selected to induce a specific emotion in the user). The user is prompted to suppress the emotion invoked by the image, and the camera is operably configured to enable a measure of suppression in accordance with the user's real-time facial response. Certain systems and methods of the present disclosure may comprise presenting one or more instances of CSIs comprising emotional stimulus with an emotional suppression instruction 1100 within an Emotional Expression Training platform or platform-product.

Figure 12:
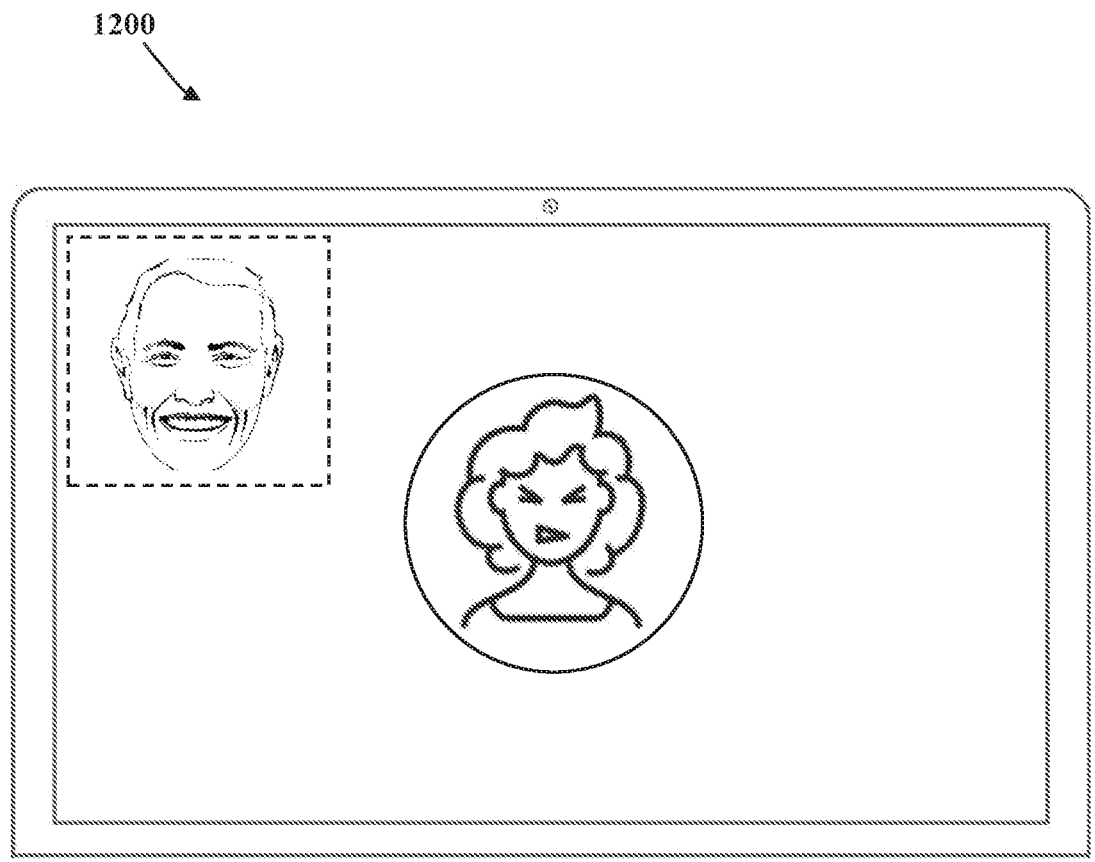
FIG. 12 is a graphical user interface illustration of a CSI comprising an emotional stimulus with an emotional reappraisal instruction, in accordance with an embodiment.

FIG. 12 is a graphical user interface illustration of a CSI comprising an emotional stimulus with an emotional suppression instruction with an emotional reappraisal instruction 1200. In accordance with an embodiment, an emotional stimulus with an emotional reappraisal instruction 1200 comprises presenting to a user an image having subject matter intended to invoke an emotional reaction in the user. The image may consist of an image of a face with an emotional expression, or the image may consist of an image selected from the International Affective Picture System (IAPS) (or other subject matter selected to induce a specific emotion in the user). The user is prompted to reappraise the emotion invoked by the image into an alternative emotion, and the camera is operably configured to enable a measure of reappraisal in accordance with the user's real-time facial features. Certain systems and methods of the present disclosure may comprise presenting one or more instances of CSIs comprising emotional stimulus with an emotional reappraisal instruction 1100 within an Emotional Expression Training platform or platform-product.

The above-described embodiments can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

As will be appreciated by one of skill in the art, embodiments of the present disclosure may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A computer-implemented method for facial image processing, comprising:
    presenting, with a computing device comprising a user interface, a first instance of a computerized cognitive-bias modification regimen comprising a computerized stimuli or interaction to a user, wherein the computerized stimuli or interaction comprises an emotional expression prompt comprising an image or icon representative of at least one face displaying an emotional expression, wherein the emotional expression prompt is configured to prompt the user to distinguish a positive or negative valence for the at least one face and generate a facial expression according to the emotional expression prompt;
    receiving in real-time, with a camera operably engaged with the computing device, a digital image of the facial expression of the user in response to the emotional expression prompt;
    processing, with at least one processor, the digital image of the facial expression of the user to determine a valence input and an intensity or arousal input corresponding to the facial expression of the user in response to the emotional expression prompt;
    comparing, with the at least one processor, the valence input and the intensity or arousal input to a predetermined valence and intensity or arousal range associated with the emotional expression prompt;
    determining, with the at least one processor, a measure of concordance between the facial expression of the user and the emotional expression prompt;
    analyzing, with the at least one processor, the measure of concordance between the facial expression of the user and the emotional expression prompt to identify one or more cognitive bias in the user, wherein the one or more cognitive bias comprises at least one negatively biased perception of a neutral or ambiguous expression of the at least one face; and
    presenting, with the computing device via the user interface, one or more targeted or modified emotional expression prompt configured to target one or more specific emotions in the user,
    wherein the computerized cognitive-bias modification regimen is configured to positively improve the at least one negatively biased perception in the user.

2. The method of claim 1 further comprising determining, with the at least one processor, a measure of an affective state of the user according to the measure of concordance between the facial expression of the user and the emotional expression prompt.

3. The method of claim 1 further comprising:
    concomitantly with receiving the digital image of the facial expression of the user in response to the emotional expression prompt,
    measuring, with at least one physiological sensor, at least one physiological input of the user in response to the computerized stimuli or interaction, the measuring being performed concomitantly with the receiving of the digital image of the facial expression of the user in response to the emotional expression prompt; and
    determining, with the at least one processor, an affective state of the user based on the at least one physiological input.

4. The method of claim 2 further comprising providing, with the computing device, a second or subsequent instance of a computerized stimuli or interaction according to the measure of concordance between the facial expression of the user and the emotional expression prompt determined in the computerized stimuli or interaction.

5. The method of claim 4 further comprising modifying, with the at least one processor, the second or subsequent instance of the computerized stimuli or interaction based on the one or more cognitive bias or the measure of the affective state of the user according to the measure of concordance between the facial expression of the user and the emotional expression prompt determined in the computerized stimuli or interaction.

6. The method of claim 3 further comprising rendering, with the at least one processor, a second or subsequent instance of the computerized stimuli or interaction according to the affective state of the user based on the at least one physiological input.

7. The method of claim 5 further comprising determining, with the at least one processor, a measure of change in the one or more cognitive bias or the measure of the affective state of the user in response to the second or subsequent instance of the computerized stimuli or interaction.

8. A system for facial image processing, comprising:
    a computing device comprising a camera configured to receive a digital image of a facial expression of a user in real-time;
    an integral or remote processor communicatively engaged with the computing device; and
    a non-transitory computer readable medium having instructions stored thereon that, when executed, cause the processor to perform one or more operations, the one or more operations comprising:
        rendering a first instance of a computerized cognitive-bias modification regimen comprising a computerized stimuli or interaction to the computing device, wherein the computerized stimuli or interaction comprises an emotional expression prompt comprising an image or icon representative of at least one face displaying an emotional expression, wherein the emotional expression prompt is configured to prompt the user to distinguish a positive or negative valence for the at least one face and generate a facial expression according to the emotional expression prompt;

receiving a real-time digital image of a facial expression of a user in response to the emotional expression prompt;

processing the digital image to determine a valence input and an intensity input corresponding to the facial expression;

comparing the valence input and the intensity input to a predetermined valence and intensity range associated with the emotional expression prompt;

determining a measure of concordance between the facial expression of the user and the emotional expression prompt;

analyzing the measure of concordance between the facial expression of the user and the emotional expression prompt to identify one or more cognitive bias in the user, wherein the one or more cognitive bias comprises at least one negatively biased perception of a neutral or ambiguous expression of the at least one face; and presenting one or more targeted or modified emotional expression prompt configured to target one or more specific emotions in the user, wherein the computerized cognitive-bias modification regimen is configured to positively improve the at least one negatively biased perception in the user.

9. The system of claim 8 further comprising at least one physiological sensor operably engaged with the processor to measure at least one physiological sensor input in response to the computerized stimuli or interaction, wherein the at least one physiological sensor comprises an EEG and the at least one physiological sensor input comprises EEG measurements of the user, and wherein the one or more operations further comprise monitoring changes in the EEG measurements of the user in response to the computerized stimuli or interaction to determine a level of change in cognition, affect, and/or bias of the user.

10. The system of claim 8 wherein the one or more operations further comprise determining a measure of an affective state of the user according to the measure of concordance between the facial expression of the user and the emotional expression prompt.

11. The system of claim 10 wherein the one or more operations further comprise rendering a second or subsequent instance of a computerized stimuli or interaction according to the measure of concordance between the facial expression of the user and the emotional expression prompt.

12. The system of claim 11 wherein the one or more operations further comprise modifying the second or subsequent instance of the computerized stimuli or interaction according to the one or more cognitive bias or the measure of the affective state of the user.

13. The system of claim 9 wherein the one or more operations further comprise modifying the computerized stimuli or interaction according to the at least one physiological sensor input.

14. The system of claim 12 wherein the one or more operations further comprise determining a measure of change in the one or more cognitive bias or the measure of the affective state of the user in response to the second or subsequent instance of the computerized stimuli or interaction.

15. A non-transitory computer-readable medium encoded with instructions for commanding one or more processors to execute operations of a method for facial image processing, the operations comprising:

rendering a first instance of a computerized cognitive-bias modification regimen comprising a computerized stimuli or interaction to an output device, wherein the computerized stimuli or interaction comprises an emotional expression prompt comprising an image or icon representative of at least one face displaying an emotional expression, wherein the emotional expression prompt is configured to prompt the user to distinguish a positive or negative valence for the at least one face and generate a facial expression according to the emotional expression prompt;

receiving a digital image of the facial expression of the user in response to the emotional expression prompt;

processing the digital image to determine a valence input and an intensity input corresponding to the facial expression;

comparing the valence input and the intensity input to a predetermined valence and intensity range associated with the emotional expression prompt;

determining a measure of concordance between the facial expression of the user and the emotional expression prompt;

analyzing the measure of concordance between the facial expression of the user and the emotional expression prompt to identify one or more cognitive bias in the user, wherein the one or more cognitive bias comprises at least one negatively biased perception of a neutral or ambiguous expression of the at least one face; and presenting one or more targeted or modified emotional expression prompt configured to target one or more specific emotions in the user, wherein the computerized cognitive-bias modification regimen is configured to positively improve the at least one negatively biased perception in the user.

16. The method of claim 3 further comprising measuring, with the at least one processor communicably engaged with the at least one physiological sensor, the at least one physiological sensor input in response to the computerized stimuli or interaction, to determine a measure of cognition, affect, and/or bias of the user, wherein the at least one physiological sensor comprises an EEG sensor.

17. The system of claim 8 wherein the emotional expression prompt comprises an image or icon representative of a composite face having two or more conflicting expressions, and wherein providing the computerized stimuli or interaction comprises prompting the user to distinguish between the two or more conflicting expressions of the composite face.

18. The method of claim 3 further comprising:
monitoring changes in the physiological input of the user in response to the emotional expression prompt; and
determining a measure of cognition, affect, and/or bias of the user based on the changes in the physiological input.

19. The method of claim 1 wherein the emotional expression prompt comprises an image or icon representative of a composite face having two or more conflicting expressions, and wherein providing the computerized stimuli or interaction comprises prompting the user to distinguish between the two or more conflicting expressions of the composite face.

* * * * *